US007085746B2

(12) United States Patent
Cordery et al.

(10) Patent No.: US 7,085,746 B2
(45) Date of Patent: Aug. 1, 2006

(54) METHOD AND SYSTEM FOR NOTIFYING MAIL USERS OF MAIL PIECE CONTAMINATION

(75) Inventors: Robert A. Cordery, Danbury, CT (US); Karin A. Russo, Redding, CT (US); Ronald P. Sansone, Weston, CT (US)

(73) Assignee: Pitney Bowes Inc., Stamford, CT (US)

(*) Notice: Subject to any disclaimer, the term of this patent is extended or adjusted under 35 U.S.C. 154(b) by 615 days.

(21) Appl. No.: 09/683,381

(22) Filed: Dec. 19, 2001

(65) Prior Publication Data

US 2003/0115161 A1 Jun. 19, 2003

(51) Int. Cl.
*G06Q 50/00* (2006.01)

(52) U.S. Cl. .......... 705/408

(58) Field of Classification Search .......... 705/401, 705/400, 404, 406, 407, 408, 410; 209/584; 235/375; 382/101
See application file for complete search history.

(56) References Cited

U.S. PATENT DOCUMENTS 5,089,395 A 2/1992 Snyder et al. .......... 435/39
5,200,626 A * 4/1993 Schultz et al. .......... 250/390.04
5,440,136 A * 8/1995 Gomberg .......... 250/390.04
5,902,385 A 5/1999 Willeke et al. .......... 96/316
5,904,752 A 5/1999 Willeke .......... 96/216
6,271,154 B1 8/2001 Shen et al. .......... 438/725
6,567,008 B1 5/2003 Sansone
2002/0124664 A1* 9/2002 Call et al. .......... 73/863.22
2002/0141613 A1* 10/2002 Sansone .......... 382/101
2003/0034874 A1* 2/2003 Mann .......... 340/5.3
2003/0062414 A1 4/2003 Tsikos et al.
2003/0072469 A1* 4/2003 Alden .......... 382/101
2003/0110048 A1 6/2003 Sansone
2003/0110135 A1 6/2003 Sansone
2003/0110143 A1 6/2003 Sansone
2003/0110144 A1 6/2003 Sansone
2003/0110145 A1 6/2003 Sansone
2003/0113230 A1 6/2003 Cordery et al.
2003/0113922 A1 6/2003 Cordery et al.
2003/0136203 A1* 7/2003 Yoon .......... 73/864.33

FOREIGN PATENT DOCUMENTS

DE 10153420 A1 * 6/2002
EP 1063602 A1 * 12/2000

OTHER PUBLICATIONS

Unknown Author, “Scanna Mail”, Spring 2001, 5 pages, available at www.scanna-msc.com.*
Unknown Author, ECIL venture offers portable scanner—Expects further orders, Nov. 2001, Business Line, 2 pages.*

(Continued)

*Primary Examiner*—Thomas A. Dixon
(74) *Attorney, Agent, or Firm*—George M. Macdonald; Steven J. Shapiro; Angelo N. Chaclas

(57) ABSTRACT

A method and system for notifying users of a mail system that a mail piece has been quarantined is provided. A plurality of incoming mail mailboxes each include a sampler to sample air from a letter that is tested using a first sensor. Source information corresponding to hazard flagged mail pieces and other quarantined mail is utilized to notify the affected users of the mail system.

17 Claims, 10 Drawing Sheets

700
QUARANTINE NOTIFICATION
710 DETECT HAZARD AT FIRST MAILBOX
720 FIRST MAILBOX NOTIFIES SERVER OF HAZARD AND PROVIDE SCAN DATA
730 SERVER DETERMINES NOTIFICATION CONTACT METHOD
740 SERVER COMMUNICATES NOTIFICATION
END

OTHER PUBLICATIONS

U.S. Appl. No. 09/683,380 entitled Method and System for Detecting Biological and Chemical Hazards in Networked Incoming Mailboxes.
U.S. Appl. No. 09/683,379 entitled Method and System for Detecting Biological and Chemical Hazards in Mail.
"Mail Performation Paddle used during a Yellow Fever Epidemic", http://www.si.edu/postal/learnmore/paddle.html, Nov. 29, 2001, 2 pages.
"The bugs of war", Nature, vol. 411, May 17, 2001, 4 pages.
Pinnick, R.G., et al., "Real-time Measurement of Fluorescence Spectra from Single Airborne Biological Particles", 1999, 32 pages.
SKC BioSampler brochure, 4 pages.
Hohnson-Winegar, A., et al., "The DoD Biological Detection Program, NDIA Roundtable Discussions", Oct. 24, 2000, 27 pages.
"Anthrax Detectors ar coming", Office of Naval Research, Oct. 29, 2001, 1 page.
Ocean Optics Brochure, Endospore Detection, Dec. 5, 2001, www.oceanoptics.com, 4 pages.
Shanker, M.S., "Instant anthrax detector developed in Hyderabad", Nov. 5, 2001, 1 page.
Introduction to Fluorescense Techniques with bibliography, Dec. 4, 2001, www.probes.com/handbook, 9 pages.
Cao, et al., DNA Nanoparticle Assembly and Diagnostics, Dec. 4, 2001, 2 pages.
Ocean Optics Portable Endoscope Detection System Offers Real-time Antrax Screening, Nov. 15, 2001, 1 page.
Scholl, et al., "Immunoaffinity-based phosphorescent sensor platform for the detection of bacterial spores", abstract Apr. 2000, 1 page.
"What is a Fluorometer?", Jul. 17, 2001, 1 page, http://response.restoration.noaa.gov/oilaids/SMART/SMART-tour/fluor.html.
Hargis, et al., "Ultraviolet fluorescence indentification of protein, DNA and bacteria", abstract Feb. 1995, 1 page.
McMillan, "Point-of-care Real Time Molecular Detection of Infectious Agents" May 20, 2001, 2 pages.
"Cellomics, Inc. Announces the Development of Biowarfare Detection Methods", Nov. 21, 2001, www.prnewswire.com, 1 page.
"Lambda Technologies' Variable Microwave Systems Adapted to 'Zap' Bioterrorism Threat", Nov. 5, 2001, www.prnewswire.com, 2 pages.
"Egea Awarded Second DARPA Contract to Fight Bioterrorism", Oct. 30, 2001, 1 page.
Meserve, J., "Feds, industry rush to make cheap biohazard detectors", Nov. 1, 2001, 1 page.
"Mathematical model provides new tool to asses mail-bourne spread of anthrax" May 13, 2002, 2 pages.
"UMAss chemist working on sensors that could eventually identify bioterror agents", Dec. 13, 2001, 2 pages.
"Stickers warn of UV Radiation", May 23, 2000, 1 page.
"Simple and inexpensive, an artificial nose senses smell by seeing colors", Aug. 16, 2000, 1 page.
"Electronic Sniffer, Listen Hard and listen good if you want to name that smell", Dec. 19, 200, 1 page, www.newscientist.com.
E-nose noses out mines, Office of Naval Research, Apr. 17, 2001, 1 page.
"On a spot smaller than a dime, UB chemists print sensors that may detect hundreds of chemicals", Jan. 25, 2002, 2 pages.
"The Classica Group Files Patent Application for its Method of Sterilization Against Anthra Bacteria Disseminated on or in Paper", Oct. 26, 2001, businesswire, 1 page.
Gordon, M., "Companies accused of Anthrax Fraud", Nov. 15, 2001, 1 page.
"Sensors Detect Biological Weapons", www.photonics.com/content/Jan99/techWeapons.html, Jan. 1999, 4 pages.
Aston, C. ,"Biological Warfare Canaries", IEEE Spectrum, Oct. 2001, 6 pages.
Murray, C., Biodetectors aim to broaden search for anthrax bacteria, Oct. 15, 2001, 5 pages.
"Biosensors and Biochips for Environmental and Biomedical Applications", www.ornl.gov/virtual/biosensors, Dec. 4, 2001, 2 pages.
"ID Mail Systems to Develop Mail Profiling System for in-bound Mail Centers Against Potential Threatening Mail", Oct. 18, 2001, 2 pages.
"Mailrooms on Front Lines in Bioterrorism Fight", Oct. 15, 2001, The Wall Street Journal, 1 page.
Vorenberg, S., "Sandia designs sensors to detect toxic chemicals in water", Oct. 12, 2001, www.abqtrib.com, 2 pages.
"Sandia's soil and groundwater chemical 'sniffer' may help protect the nation's water supply", Oct. 3, 2001, www.sandia.gov/media/NewsRel.NR2001/whtsniff.htm (4 pages).
"Two new Sandia 'sniffers' expand law enforcement abilities to detect explosives and narcotics", Nov. 30, 1999, www.sandia.gov/media/NewsRel.NR1999/sniffers.htm (4 apges).

* cited by examiner

A
C
330
E
342
340
150
100
322
F
D

D
320
300
330
100
B
340
324
332
330
322
334
C
A

METHOD AND SYSTEM FOR NOTIFYING MAIL USERS OF MAIL PIECE CONTAMINATION

CROSS REFERENCE TO RELATED APPLICATIONS

This application is related to commonly assigned, co-pending U.S. patent application Ser. No.: Not Yet Assigned, filed on even date herewith, entitled "METHOD AND SYSTEM FOR DETECTING BIOLOGICAL AND CHEMICAL HAZARDS IN MAIL," in the name of Robert A. Cordery, Ronald P. Sansone and Karin A. Russo, assigned Ser. No. 09/683,379 the disclosure of which is hereby incorporated by reference in its entirety. This application is related to commonly assigned, co-pending U.S. patent application Ser. No.: Not Yet Assigned, filed on even date herewith, entitled "METHOD AND SYSTEM FOR DETECTING BIOLOGICAL AND CHEMICAL HAZARDS IN NETWORKED INCOMING MAILBOXES," in the name of Ronald P. Sansone, Robert A. Cordery and Karin A. Russo, assigned Ser. No. 09/683,380 the disclosure of which is hereby incorporated by reference in its entirety.

BACKGROUND OF INVENTION

The embodiments described herein relate generally to detecting hazards in mail and more specifically to systems and methods for detecting and containing contaminated mail in an incoming mail mailbox.

The United States Postal Service (USPS) provides a service of mail piece reception, sorting and delivery to national addresses and international postal streams. The USPS processes approximately 200 billion domestic letters per year. The USPS also processes parcels. Similarly, other courier services also exist that process letters and parcels.

Anthrax spores have been detected on mail pieces, mail-handling equipment and in or near areas where certain mail pieces that likely contained anthrax were handled. Several people that were in such areas have contracted anthrax disease. These attacks pose a danger of infection that may be lethal to those in affected areas. Additionally, there is no readily available warning system to provide an early warning that a mail piece contains anthrax spores. Certain members of the general population may fear receiving and handling mail due to the threat of mail terrorism.

Anthrax is a biological agent that has apparently been placed in the U.S. postal delivery system in mail pieces that could be considered camouflaged as ordinary mail because they were not properly marked or properly contained, as a dangerous biological agent should be. The person placing such mail in the mail system had the apparent sole purpose of delivering the Anthrax as a biological weapon to kill the immediate victims and terrorize others who use the postal system. The Anthrax has apparently been transported in spore form and in such a small form as to enable it to float in the air. The disease known as Anthrax disease is caused by the bacterium Bacillus anthracis that is known as Anthrax. Anthrax is rod-shaped, and relatively large for a bacterium at 1 to 10 μm in length.

The disease may be manifested as pulmonary anthrax or inhalation anthrax when a sufficient amount of Anthrax is inhaled. The disease may be manifested as intestinal anthrax when ingested in too great a quantity. The disease may be manifested as cutaneous anthrax that is typically found when an open wound or sore of a person has been exposed to Anthrax.

There are dozens of biological and chemical substances that are potential hazards if placed in the mail stream. Additionally, explosive devices have been sent in the mails in order to harm recipients.

SUMMARY OF INVENTION

In one embodiment, a plurality of incoming mail receptacle device includes a biological contamination detection system to determine if mail inserted into the receptacle is contaminated. An air sample is collected from an incoming mail piece and then processed though a hazard detector to determine if the mail piece is contaminated. A mail piece source indication is detected from each mail piece. In the event of a hazard detection indication at one incoming mail receptacle, notification information for all quarantined mail pieces in the mail receptacle is transferred to a server that sends notification information to the users.

DETAILED DESCRIPTION

Anthrax has been introduced into the mail system as a biological weapon. Similarly, other hazardous biological or chemical materials might be similarly transported in a mail system. Such criminal and terrorist activity provides a threat of cross contamination if entered into the mail-processing stream.

The present application describes embodiments of a system and method for detecting contaminated mail at the point of entry to keep it from entering the mail stream. The United States Postal Service (USPS) is referred to describe illustrative examples of a mail streams. The embodiments are illustrative and where alternative elements are described, they are understood to fully describe alternative embodiments without repeating common elements of other appropriate embodiments.

There are many incoming mail receptacle in use. For example, in the United States, the USPS makes available many incoming mailboxes situated on public streets. Additionally, some public mailboxes are designed to be accessible to a driver such that the driver does not have to leave the car to place mail into the mailbox. Furthermore, USPS Post Offices utilize mail slots to receive incoming mail. Similarly, apartment buildings often have a group outgoing mail receptacle. Mail carriers also pick up mail from residential mailboxes. There are also several types of office mail delivery outgoing mailboxes in use. A department typically has a mail stop area with a drop off area for mail to be delivered to a post office.

Anthrax bacteria, bacillus antrhracis, has been described as a very large, Gram-positive, spore-forming rod of 1–1.2 micron in width and 3–5 micron in length that form oval spores located centrally in a non-swollen sporangium. Typical paper has pores that average 10 microns in diameter, while the width of a typical human hair is around 90 microns. Letter envelopes are often not hermetically sealed and may be porous such that anthrax may pass through the envelope. Accordingly, anthrax and other biological and chemical hazards may escape from envelopes to contaminate mail-processing equipment that may cross contaminate other letters. Therefore, a sealed letter may not confine any enclosed anthrax to that particular letter and anthrax or other hazards may adhere to mail pieces. Some people advocate scrutinizing mail with excess postage or handwritten addresses. However, the relative anonymity of required markings on a letter present an inherent difficulty in identifying suspect letters to be scrutinized on the basis of the identity of the sender, receiver, type of markings used or postage.

Figure 1:
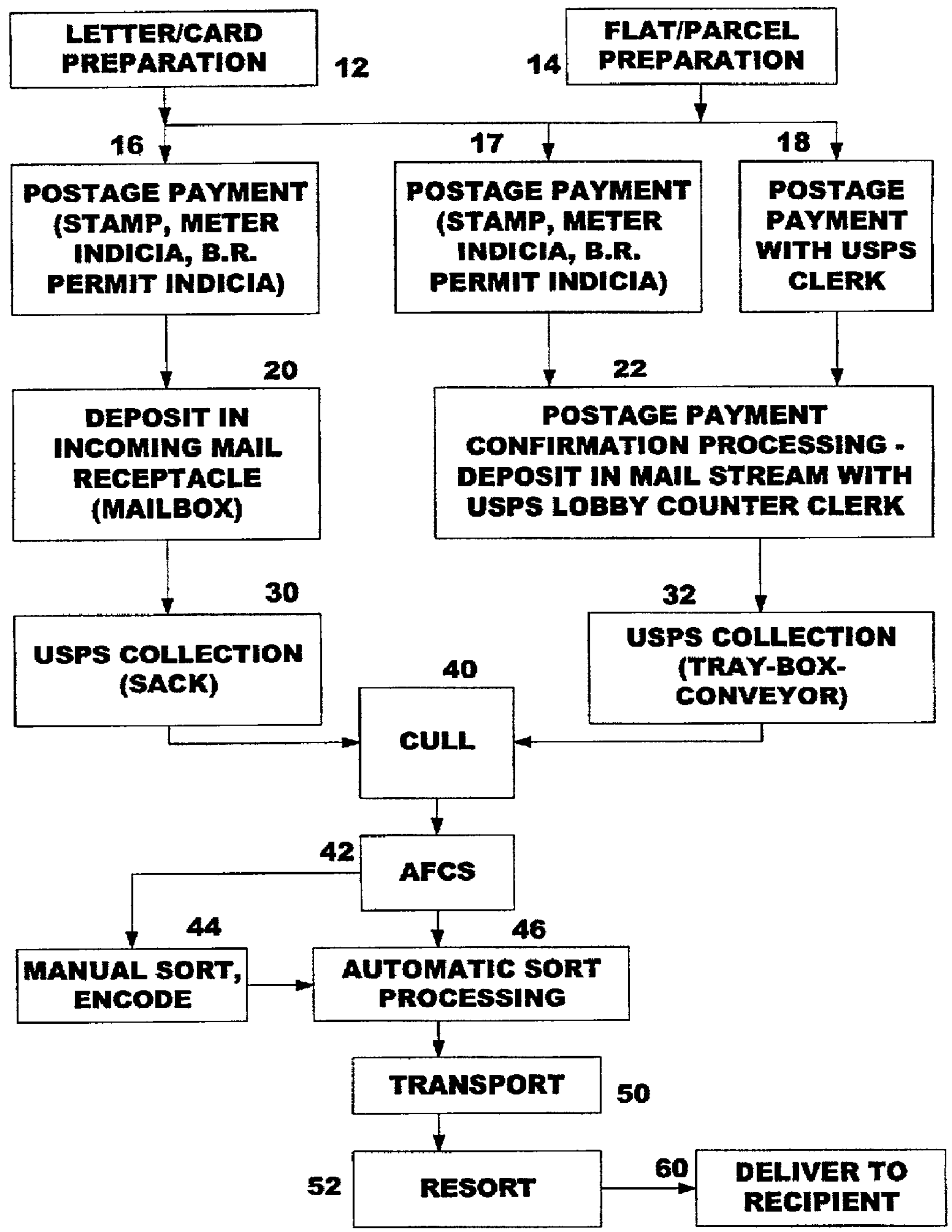
FIG. 1 is a flow chart showing a prior art postal delivery process.

Referring to FIG. 1, a prior art mail process is shown. In step 12, a mail system user will prepare a mail piece such as a letter or a card. The user may place postage on the mail piece using a stamp, meter indicia or permit indicia in step 16. The user then places the mail piece in an incoming mail receptacle such as an incoming USPS mailbox in step 20. A user may also place postage on the mail piece in step 17 and then bring the mail piece to a USPS clerk in step 22. A postal worker will collect mail pieces from the mailbox in a sack in step 30 and bring them to a USPS facility for an initial cull in step 40. The mail pieces will then go through an AFCS process in step 42 to scan, OCR and code the mail pieces. If the mail piece could not be processed by the AFCS, a manual sort and encode is performed in step 44. Thereafter in step 46 the AFCS and manual streams merge for automatic sort processing in step 46. Thereafter the sorted mail is transported in step 50 to a USPS facility where it is resorted for a letter carried in step 52 and delivered to the recipient in step 60. The user may prepare a flat or parcel in step 14. The user may place postage on the mail piece in steps 16 or 17, but may pay for postage applied by a clerk in step 18. The flat or parcel may be placed in a mailbox in step 20 as described above, or may be brought to a USPS clerk in step 22 for processing into a incoming tray in step 32. The mail piece is then placed in the initial cull in step 40 and processed as above.

Figure 2:
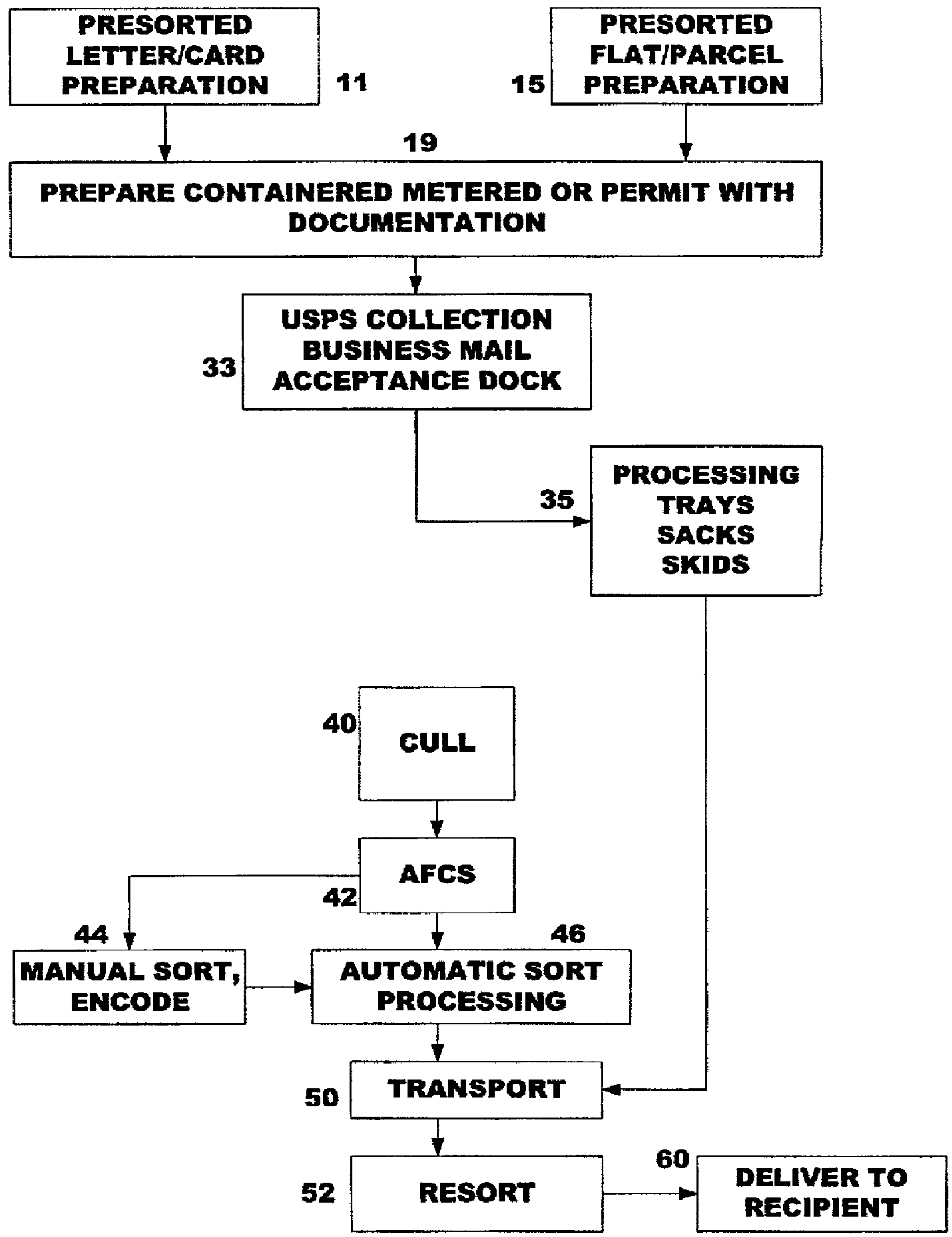
FIG. 2 is a flow chart showing a prior art postal delivery process.

Referring to FIG. 2, a prior art mail process for presorted bulk mail is shown. In step 11, a mail system user prepares presorted mail pieces such as letter and cards. The user may prepare presorted flats or parcels in step 15, the mail pieces are prepared with permit indicia or metered indicia with the required presort discount documentation in step 19. The mail pieces are brought to the USPS business mail acceptance dock with the required documentation in step 33 to be placed in processing trays, sacks and skids in step 35. As shown in FIG. 2, the mail is placed directly in transport in step 50 for later resort and delivery.

Figure 3A:
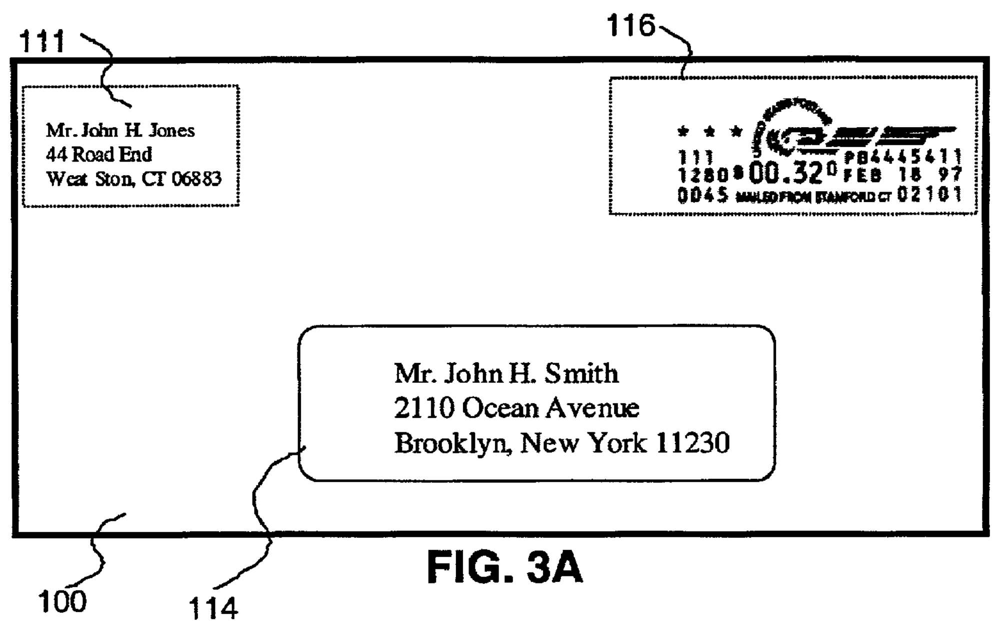
FIG. 3A is a top view of a mail piece.
Figure 3B:
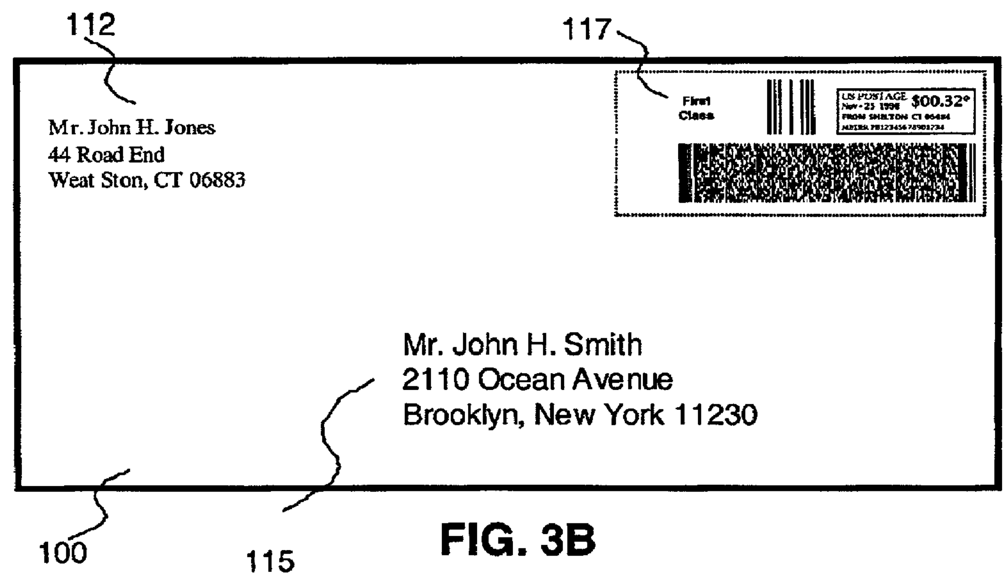
FIG. 3B is a top view of a mail piece.

Referring to FIG. 3A, an envelope is shown. Envelope 100 is marked with a label 111 for a return address and a label 114 for a destination address. A postage indicia 116 is also shown. Referring to FIG. 3B, an envelope is shown. Envelope 100 is directly marked with return address 112 and destination address 115 with postage indicia 117. The envelope is a number 10 paper envelope. The flap (not shown has a strip of glue that covers much of the perimeter of the inside flap.

The present application describes embodiments that process envelopes that are not hermetically sealed. The examination and study of many envelopes suggests that even very well sealed envelopes have four corners that are not hermetically sealed. The openings typically vary between 3 and 10 mm. Squeezing the edges of a flat envelope will deform the flat envelope into a pillow shape with air in the pillowed area. The envelope thus shaped is somewhat like a bellows such that maintaining the force on the edges while squeezing the pillowed are will force air out of the openings. If the pillow is flattened from one direction, a majority of the escaping air will come from one side of the envelope.

The force applied to the pillowed area and the edges can be monitored along with any feedback to prevent crushing the envelope.

As can be appreciated, various forms of mail include many forms of correspondence including bills, advertisements, government correspondence, periodicals and parcels.

Figure 4:
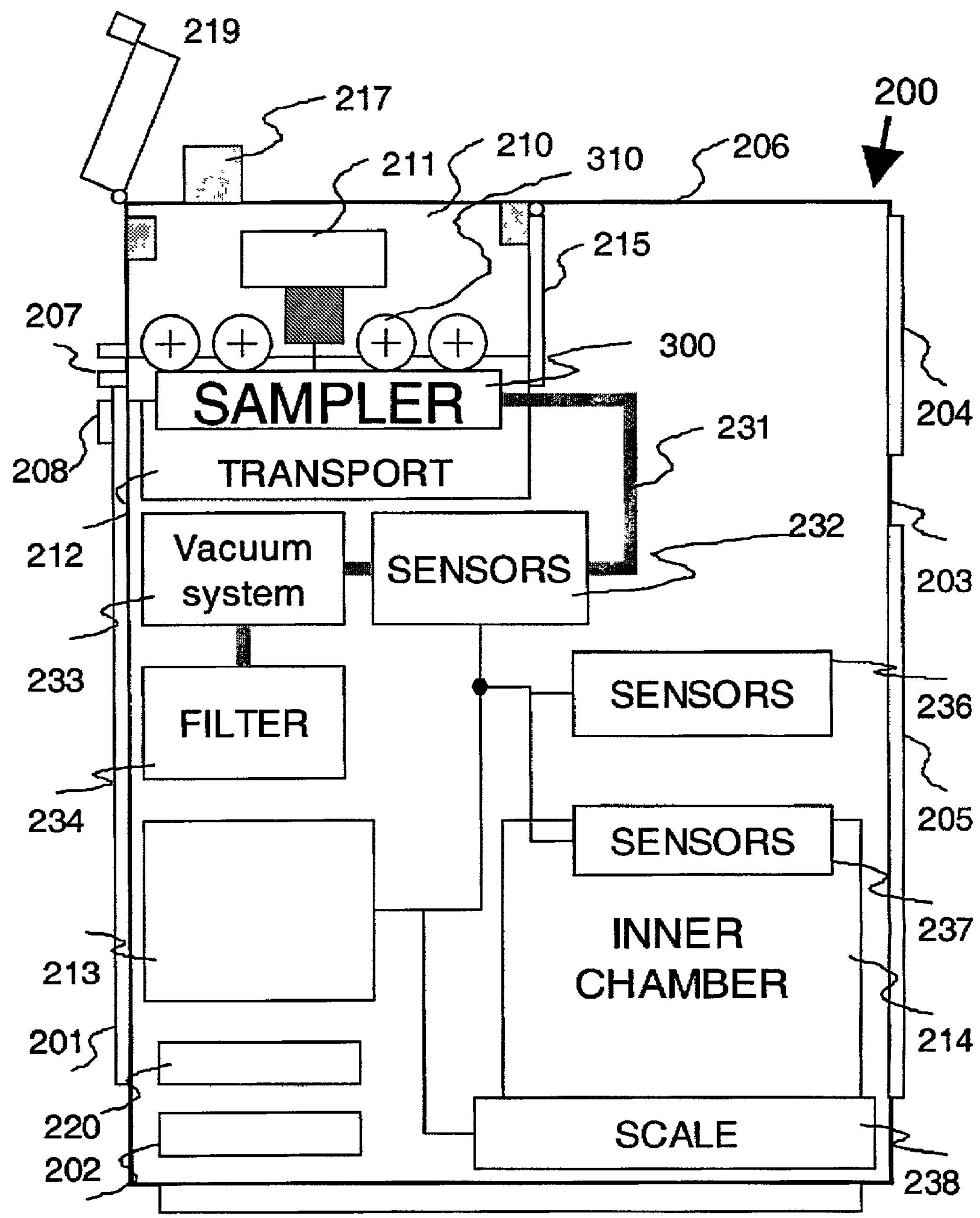
FIG. 4 is a perspective cutaway view of an incoming mail receptacle according to an embodiment of the present application.

Referring to FIG. 4, an incoming mail receptacle with hazard detector is described. Incoming mailbox 200 has a front panel 201 containing a slot 208 for receptacle identification cards and a mail slot 207 for depositing mail, a top panel 206, side panels (not shown) and a back panel 203 having a door 204 for access to life-harming materials, and a door 205 for access to non-life-harming materials. Receptacle 200 has a sampling chamber 210 that contains an image scanner 211 and a transport mechanism 212. When mail piece 100 (FIG. 5) is deposited face up in slot 207, mail piece 100 will enter sampler chamber 210. The face of mail piece 100 will be scanned and read by scanner 211 while being moved by transport 212. Receptacle controller 213 controls the hazard detection process and the hazard notification process. Controller 213 is powered by power source 202 and is connected to communications device 220. Communications device 220 includes a cellular data modem. Alternatively any wired or wireless communications device may be utilized. The control and power connections for such a system are well known and not described in detail. Power is preferably supplied by a battery and solar power array.

An external door 219 with handle is provided to allow access to mail opening 207. A second door (not shown) capable of creating an interior hermetic seal connected to the controller and provided to lock the mailbox in case a hazard is detected. An internal door 215 hermetically seals chamber 210 during the test and then after a successful test, it opens to allow the mail piece to enter the inner chamber 214. Scale 238 detects the presence and optionally the weight of the mail pieces in the inner chamber. Alternatively an optical sensor may be utilized.

The sampler described below will provide an air sample from a mail piece through vacuum tube 231 to sensors 232 using vacuum system 233 and filter 234 to vent the vacuum outside the mailbox. As described below, sensors 232 provide a near real time test that is performed before the mail piece is accepted and before the mailbox is cleared to receive another mail piece at the input 207. Additional sensors 236, 237 provide additional test having relatively longer test times. In an alternative embodiment, the mailbox stops accepting mail pieces at a predetermined time before a scheduled pick up so that the slower sensors 236, 237 can provide an adequate test. For example, if there is a scheduled pick up at 8 o'clock in the evening, the mailbox will stop accepting mail 30 minutes before to allow a PCR based DNA test of collected samples.

The mailbox is preferably hermetically sealed to contain any detected hazards and completely opaque to visible light and other near spectrums including Ultra Violet (UV) in order to prevent disruption of the sensor.

Sensors 232 include fast response sensors. Sensors 232 include an Endospore Detection System available from Ocean Optics of Dunedin, Fla. In an alternative, sensors 232 may include a laser-acoustic sensor available from the Office of Naval Research. Similarly, sensors 232 may include an ultraviolet fluorescence bacteria detector from Sandia National Laboratories described in Proc. SPIE Vol. 2366, p. 147–153, incorporated by reference.

Controller 213 will shut down the mailbox and close upon a positive test. The controller 213 will then use communications device 220 to alert a response team.

In an alternative embodiment, Sensors 232 preferably include a mass spectrometer detector for detecting explosives, narcotics, chemical and biological agents as potential hazards. Sensors 232 include a UV radiation source and a fluorometer to detect fluorescent radiation in the air sample.

In an alternative embodiment, the sampled air is forced into distilled water for 45 seconds to extract any dipicolinic acid present, followed by chelation with terbium and tested for phosphorescence.

Sensors 236 include relatively slow test systems including a 30 minute test PCR based detection system such as that available from Cepheid. The sampled air is divided via sampling tubes into the reagent chambers of the test kit and processed. Alternatively, a DNA test system available from Lawrence Livermore Laboratory is utilized. Alternatively, a system from the Office of Naval Research utilizing lasers and acoustic sensors is utilized.

Alternatively, the sampled air is forced into water and tested with water test systems such as those available from Sandia National Laboratories of Albuquerque, N. Mex.

Sensors 237 include relatively slow test systems including a toxic agent sniff sensor available from Sandia National Laboratories of Albuquerque, N. Mex. and used for testing for toxins in water supplies. In an alternative, an Immunoaffinity-based phosphorescent sensor is utilized as described in Proc. SPIE Vol. 3913, p. 204–14, incorporated by reference. In another alternative, a system available from Egea Biosciences of San Diego, Calif. is used. It was developed under a DARPA contract using a DNA-chip and non-repeating markers as identifiers of biological hazards. In another alternative, a system available from Cellomics, Inc. of Pittsburgh, Pa. using living cell technology is utilized.

In an alternative embodiment, Sensors 232 include ion mobility spectrometer sensors available from Sandia National Laboratories of Albuquerque, N. Mex. for detecting bombs.

The sampler system may be utilized in other devices that may be utilized at different stages of the mail flow process. Sensors 232, 236 and 237 are described as plural sensors, however, one sensor may be used for each. Furthermore, each sensor device described may be preferred for a sensor in device 232, 236 or 237, but may be used in any or all of the sensors 232, 236 and 237. An additional embodiment may use only one of sensors 232, 236, 237 or a combination of two or more of them.

Figure 5A:
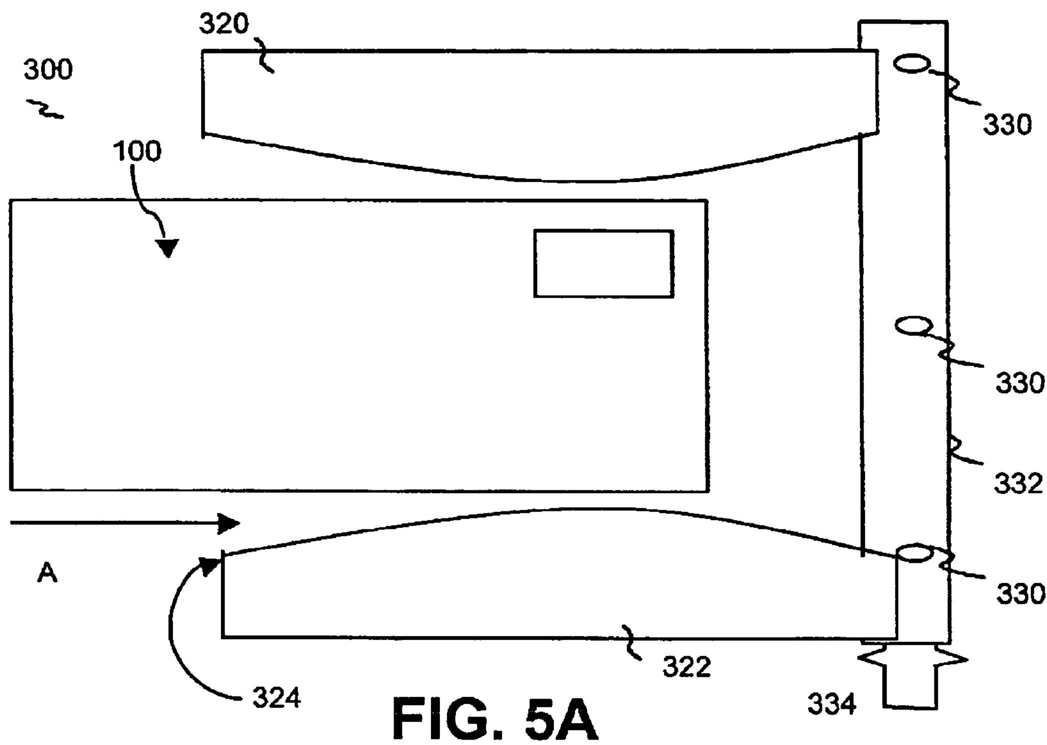
FIG. 5A is a top view of an incoming mail air sampler according to an embodiment of the present application in a first position.

Referring to FIGS. 5A–5D, the sample extractor 300 is described. Referring to FIG. 5A, a first position of the extractor includes a first envelope deforming block 320 and a second envelope deforming block 322 configured to receive a mail piece in a flat orientation that is not raised on edge. The blocks 320, 322 are shown in the open position. The mail piece is fed into the sample extractor using mail piece handling equipment such as a continuous belt driven by an electric motor. Alternatively rollers may be used. Equipment for moving mail pieces is well known and will not be described in detail. The mail piece, number 10 envelope 100 is fed into sample extractor 300 in direction A. Sample extractor 300 includes a vacuum collector 332 having openings 330 and vacuum tube 334.

Figure 5B:
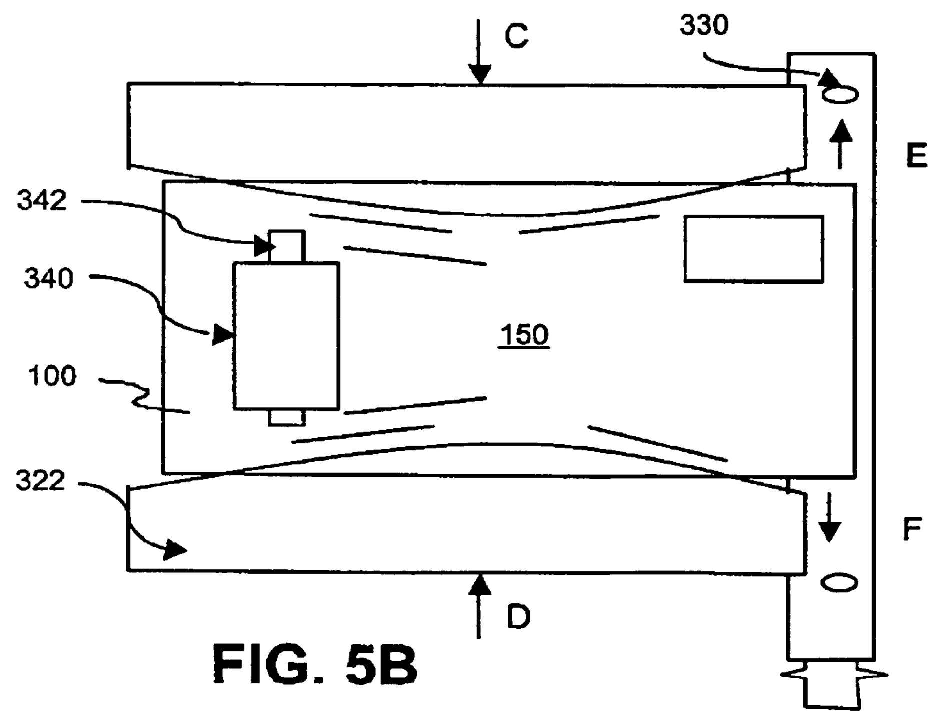
FIG. 5B is a top view of an incoming mail air sampler according to an embodiment of the present application in a second position.

Referring to FIG. 5B, a second position of the extractor is shown. When a sensor (not shown) determines that the envelope 100 is in place, block 320 is activated and forced in direction C and block 322 is forced in direction D such that edge 324 deforms envelope 100. The envelope 100 will form a pillowed area 150. Flattener 340 is a squeeze roller rubber wheel on shaft 342 that is lowered into position over envelope 100 at the edge closest the input of mailbox 200. The vacuum may begin at ports 330 as air may flow in directions E, F when at this position.

Figures 5C, 5D:
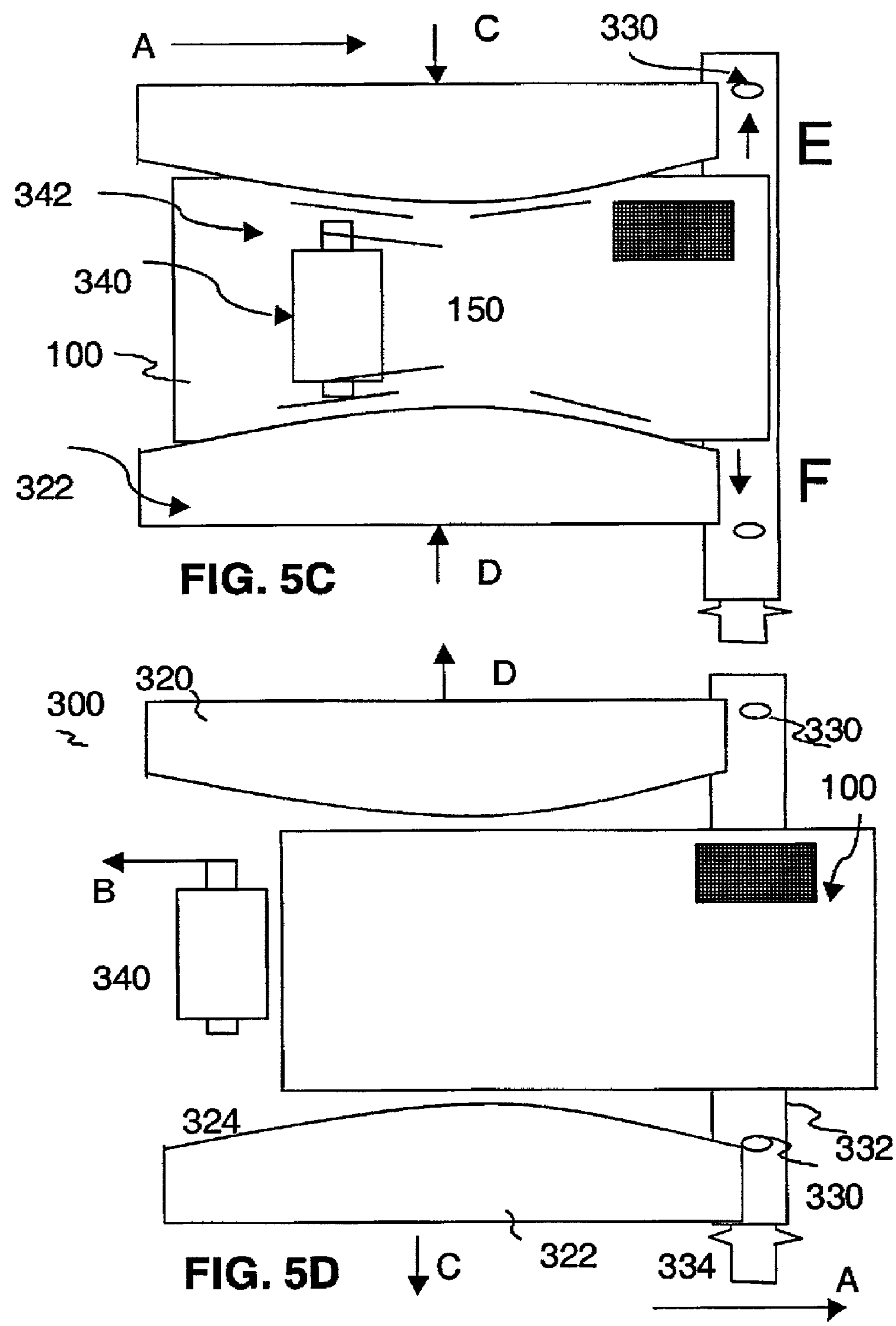
FIG. 5C is a top view of an incoming mail air sampler according to an embodiment of the present application in a third position.
FIG. 5D is a top view of an incoming mail air sampler according to an embodiment of the present application in a fourth position.

Referring to FIG. 5C, a third position of the extractor is shown. The flattener 340 is rolled forward in direction A to squeeze the air out of pillowed area 150 while the vacuum collection ports 330 collect air forced out at E, F.

In a further alternative embodiment, the squeeze roller 340 is equipped with a feedback sensor to determine if a hermetically sealed envelope is present. The force required to deflate the pillowed area 150 should decrease if the envelope 100 is not hermetically sealed. In such a case, the detected hermetically sealed envelope is segregated for further scrutiny.

In another alternative embodiment, a vacuum is applied to all or part of the bottom of the envelope to hold down the bottom side. Any air picked up by the vacuum is fed through the detector, as the envelope may be porous to a hazardous material.

Referring to FIG. 5D, a fourth position of the extractor is shown. The blocks 320, 322 are returned to the start position to release the pillowing tension on the envelope 100. The flattener 340 is rolled backward in direction B to re-flatten the envelope. The envelope is fed forward if the test passes and the flattener is then returned to a start position for the next envelope. In an alternative, the squeeze roller does not flatten the envelope o the return path B, but is lifted off the envelope.

In an alternative embodiment, only one envelope-deforming block is movable. In another alternative, the mail piece is fed on edge such that gravity will aid registration of the mail piece and collection of the sample.

In a further alternative embodiment, the width of the incoming mail piece is measured to set the position and distance between blocks 320, 322 in a snug open position before moving them into a pillowing position. The width measurement is performed using a series of light sensors in a row at the opening 207 of the mailbox 200.

Figure 6:
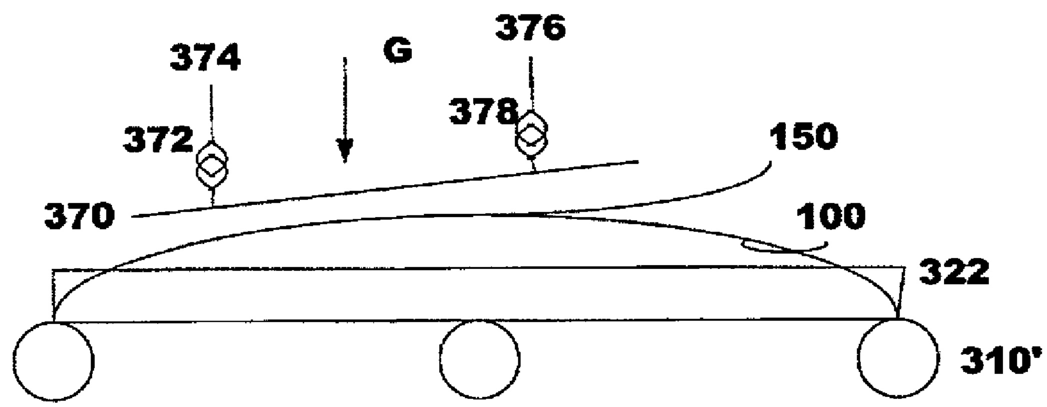
FIG. 6 is a perspective side view of an incoming mail air sampler according to an embodiment of the present application.

Referring to FIG. 6, an alternative flattener is shown. In this embodiment, flattening plate 370 is forced down in direction G by link 374 and force measurement device 372, followed by force on link 376 and force measurement device 378 to flatten pillowed area 150. In this embodiment, rollers 310' feed the envelope 100 forward into blocks 320, 322.

Figure 7:
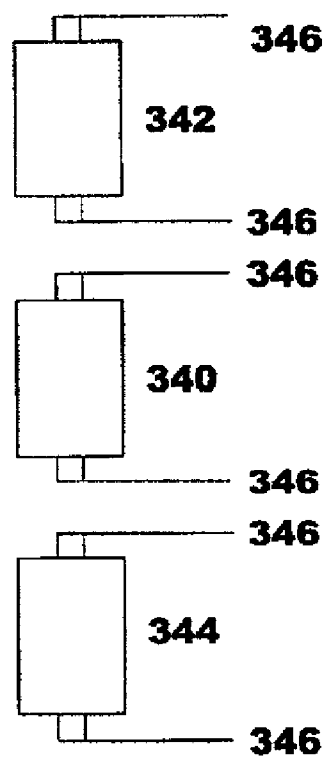
FIG. 7 is a top view of a flattener according to an embodiment of the present application.

Referring to FIG. 7, an alternative flattener is shown to accommodate varying width mail pieces. Flattener 340 is independently connected with links 346 such that any one, all, or combination of rollers 340, 342, 244 may be lowed and rolled over a mail piece.

In another embodiment, a brush or scraper is used to sample a surface or both sides of a mail piece. A source of forced air such as a fan may be used to move the sample closer to the vacuum sampling holes.

Figure 8:
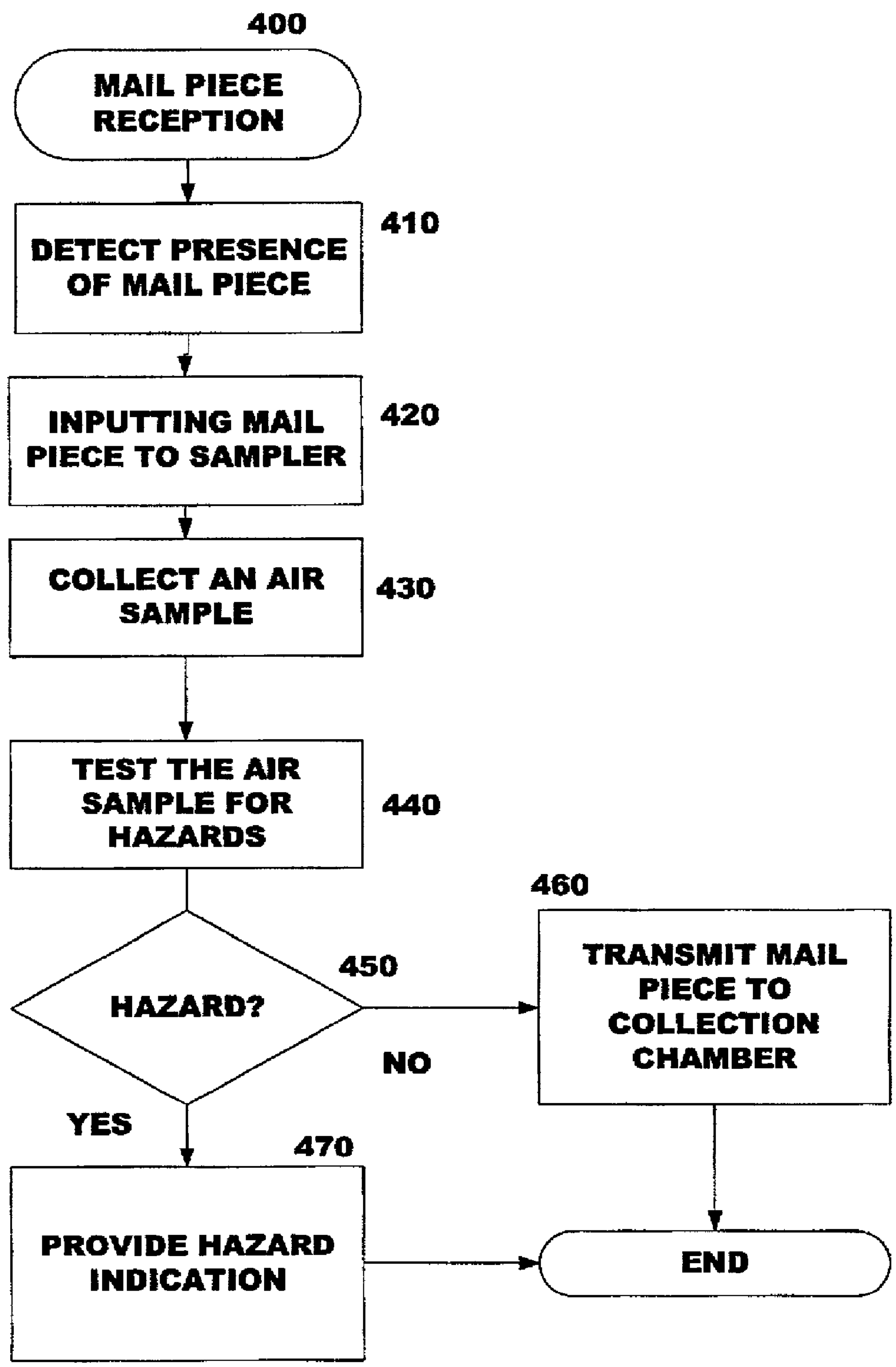
FIG. 8 is a flowchart showing a process for detecting contaminated mail according to an embodiment of the present application.

Referring to FIG. 8, a process for detecting hazardous mail is described. In step 410, the process detect the presence of a mail piece. In step 420, the process imports the mail piece into the segregated incoming mail sampler. In step 430, the process collects an air sample. In step 440, the process tests the air sample for hazards. In step 450, the process includes a decision step to decide is a hazard is present. If a hazard is present, the process provides a hazard indication in step 470 and then ends. If no hazard is present, the process transports the mail piece to the collection chamber in step 460 and then ends.

Position and presence sensors are well known and not described in detail. Similarly, force sensors and feedback loops are well known and not described in detail. Controllers and timers are well known and not described in detail. The processes described may be performed in hardware, firmware, in software on a general-purpose processor or combination thereof. The controller may be a Pentium III mobile processor with support circuits and devices, but may include another processor and may be re-configurable and may be networked via a wired or wireless communications channel.

In an alternative embodiment, USPS clerks may use the devices described above at a post office counter. In such a system, several units may be located in close proximity and may share common parts other than the actual envelope feeder. In one embodiment, a common controller may service four units that are networked. Similarly, a common vacuum source and a common power source may be shared.

In an alternative embodiment, a mailbox 200 includes an incoming chute that directs mail into a plastic bag that the postal worker can hermetically seal for transport to a safe mail handling facility to test for hazards. The mailbox identifier can be placed on the plastic bag. In another embodiment, the mailbox contains a store of plastic bags lining the receptacle and a heat applicator to hermetically seal the bags before a postal worker picks up the bag.

In an alternative embodiment, the incoming mail mailbox includes a parcel receptacle that contains a holding area that is hermetically sealed and segregated from the letter holding area. Current USPS requirements state that parcels weighing over one pound cannot be placed in incoming letter boxes. Another portion of the scale 238 may be utilized to ensure compliance.

In an alternative embodiment, the letter puffer or air sampler 300 includes a feedback system to determine if the letter is hermetically sealed. The puffer sensor tests the letter. If the feedback system determines that a letter is hermetically sealed, it is passed through an UV-C ultraviolet surface decontamination system and segregated in a hermetically sealed envelope bin.

In an alternative embodiment, the air sampler includes a segmented skewer that is utilized to penetrate the mail piece. One opening forces air into the envelope at a first location and a second opening introduces a vacuum to remove a sample of air from the envelope. In a further alternative, two hollow tubes are inserted in the envelope openings to force in air and remove a sample, respectively.

In an alternative embodiment, the scanner is placed in front of the envelope feed path to scan the top of the envelope. The scanner is used to determine if the envelope is inserted face up and includes postage. If the envelope is upside down, it is ejected. If the envelope is inserted in the correct orientation, it is scanned and fed to the detector stage.

In an alternative embodiment, the scanner is used to scan the entire face of the document.

In the embodiments described below, information is shared among networked incoming mail receptacles, preferably using a central server. Additionally, if a postal authority maintains control of data from an incoming mail receptacle and other entities have relevant information, a secure link provides information interchange. As can be appreciated, more than one postal meter manufacturer may provide meter data to a meter provider or third party for use in the system.

Figure 9:
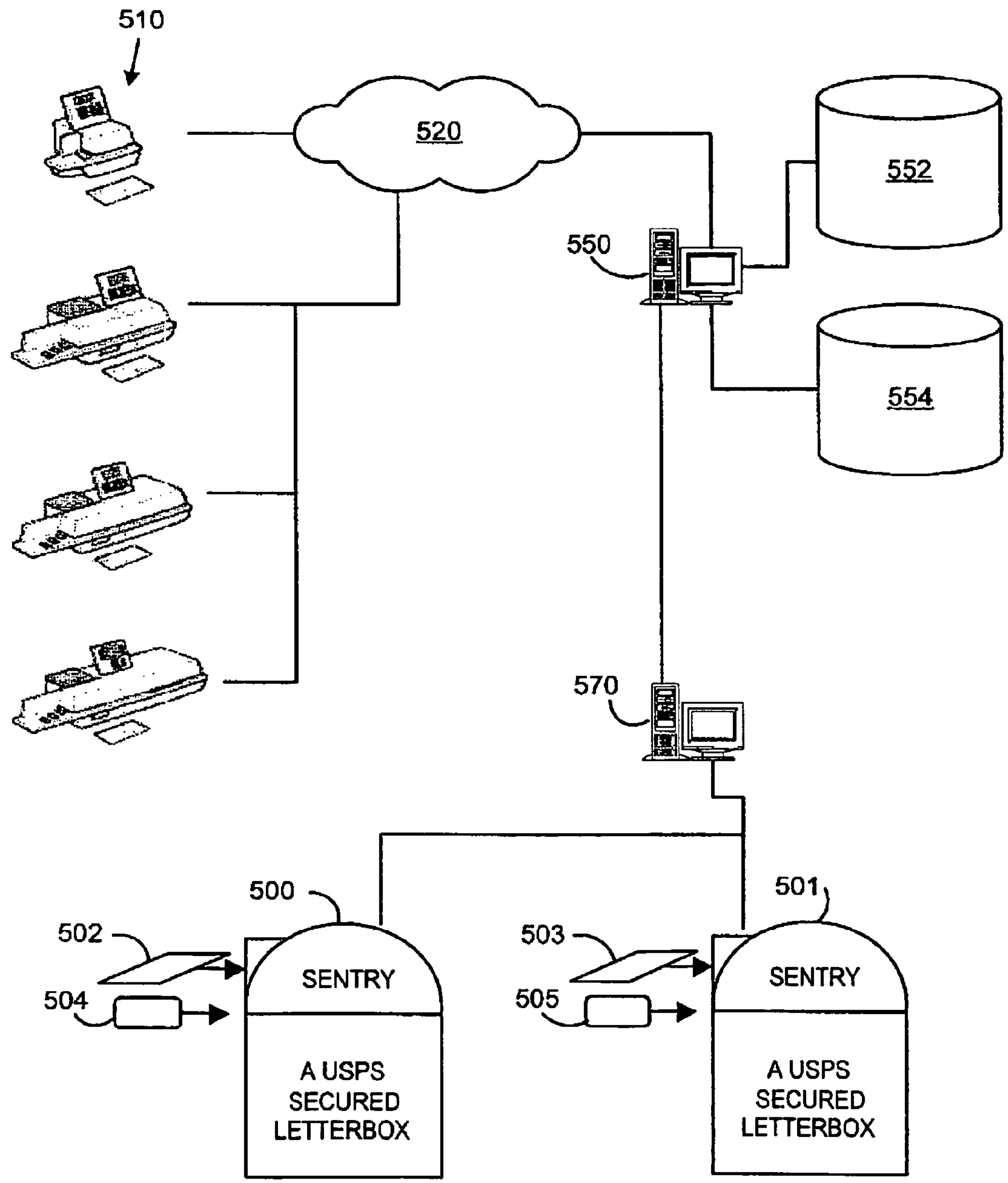
FIG. 9 is a block diagram of a networked incoming mail receptacle system according to an embodiment of the present application.

Referring to FIG. 9, a networked incoming mail receptacle system is described. Postage meters 510 are uniquely identified and located in known locations. At least some of meters 510 are connected to network 520 that is connected to trusted server 550. The network 520 is preferably a secure internet connection such as a Virtual Private Network (VPN), but could be a dial up connection, wireless connection or other wired connection. Server 550 is connected to a meter database 552 that stores meter data including service information and historical data. Database 554 includes source exclusion information. For example, database 554 includes data relating to the locations that should accept mail from a particular meter. Additionally, the database contains other source exclusion data such as counterfeit source designations, scans and handwriting analysis of known hazards, return address or destination address associated with known hazards and indicators of compromised meter numbers. Such a system provides advantageous flexibility. If a credible threat against United States Senators exists, all mail to such people and their offices will be listed as suspect and quarantined at the incoming mailboxes for further scrutiny.

Server 570 is connected to each incoming mail receptacle, 500, 501 preferably using a secure Internet connection, but LAN, WAN, wireless and wired connections can be utilized. Mail pieces 502 and 503 are tested, while users may be prompted for an identification card 504, 505 for source verification.

Database 556 includes notification information. In this embodiment, the incoming mail receptacle scans each incoming mail piece and stores the information. In one embodiment, each mailbox 500 stores a scan of each mail piece.

If a contamination hazard indication is received, the entire mailbox is physically quarantined. The mailbox 500 then uploads the current mail information to the server 550. The server determines source and destination information. For example, the server is programmed to perform an OCR of the scanned image of each envelope in the tainted mailbox.

The server will then utilize database 556 to attempt to locate a known valid email address for the sender and the recipient. If a known address is found, a notification email describing the facts of the quarantined mail including the mailbox location is sent. Optionally, the sender of the actual tainted mail is not notified. If an email address is not found, the system attempts to locate a known valid telephone number. Outside databases such as telephone directories are queried. If neither a telephone number nor an email address are available, the system prepares a postal mail notification on a post card.

In an alternative embodiment, the mailbox detects a meter number for source notification information.

Figure 10:
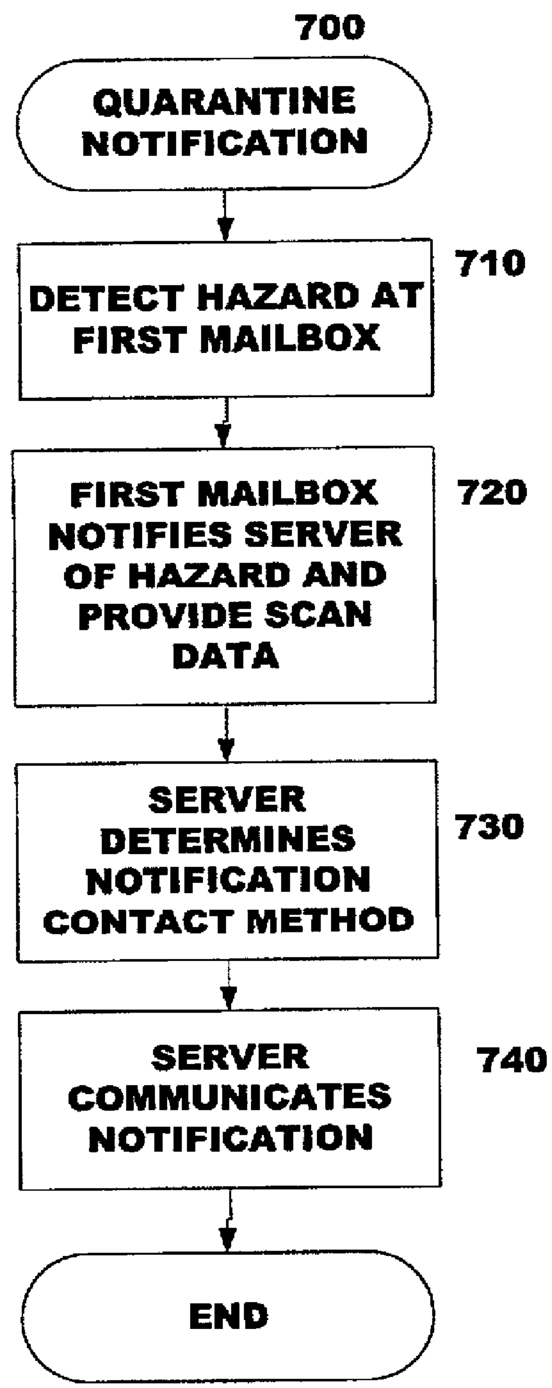
FIG. 10 is a flowchart showing a process for sharing user notification of a quarantine condition according to an embodiment of the present application.

Referring to FIG. 10, a process for notifying quarantined mail users is described. In a system of a plurality of incoming mail receptacles a first mailbox receives a hazard indication in step 710. In step 720, the first mailbox send notification to the server. The server processes the hazard notification in step 730 to determine notification data in an order of priority of email contact, telephone contact and postal mail contact. In step 740, the server sends the notification by the first available method.

The meters are preferably DM300 digital postage meter available from Pitney Bowes Inc. of Stamford, Conn., but other meters including other digital postage meters available from Pitney Bowes Inc. may be used.

The systems described above require electrical power. Power supplies are well known and not described in detail. A utility connection, a battery, solar power or other source of electricity may power the system.

The above specification describes system and methods for detecting hazards in mail. As can be appreciated, various combinations of the above detection systems may be utilized.

The described embodiments are illustrative and the above description may indicate to those skilled in the art additional ways in which the principles of this invention may be used without departing from the spirit of the invention. Accordingly the scope of the claims should not be limited by the particular embodiments described.

We claim:

1. A system of hazard detector systems for detecting hazards in a mail piece and notifying remote users including senders and recipients having quarantined mail comprising:

a plurality of detectors each including a contaminant detection hazard detector for triggering a mail piece quarantine indication, an image scanner for scanning the face of a mail piece, a communications system, and a scan detection system for providing sender and recipient information for quarantined mail pieces; and a server connected to the plurality of hazard detectors for receiving the mail piece quarantine indication and scan detection data, determining a notification method and for communicating the quarantine notification to at least one of the sender and the recipient.

2. The system of claim 1 further comprising:

a secure Internet connection between each hazard detector system and the server.

3. A method for communicating a quarantine condition to remote users including senders and recipients of a mail system having a plurality of hazard detector systems with hazard detection systems connected to a central server comprising:

detecting the presence of a mail piece;

detecting source information from the mail piece;

testing the mail piece for hazards to determine an initial mail piece quarantine condition;

alerting the central server upon detection of a hazard and providing source information to the central server;

determining a notification method; and notifying at least one user of the mail piece quarantine.

4. The method of claim 3 wherein the source detection includes detecting a destination address.

5. The method of claim 3 wherein the source detection includes detecting a return address.

6. The method of claim 3 wherein the determination of a notification method comprises determining if a valid email address is available for the user.

7. The method of claim 3 wherein the determination of a notification method comprises determining if a valid telephone number is available for the user.

8. The method of claim 3 wherein the determination of a notification method comprises determining if the mail piece address is a valid postal address for the user.

9. A mail receiving system for detecting hazards in a mail piece and notifying users including senders and recipients having quarantined mail comprising:

a plurality of mailboxes each including a contaminant detection hazard detector for triggering a mail piece quarantine indication, an image scanner for scanning the face of a mail piece, a communications system, and a scan detection system for providing source and recipient information for quarantined mail pieces; and a server connected to the plurality of mailboxes for receiving scan detection data, determining a notification method and for communicating the notification to at least one of the sender and the recipient.

10. A method for communicating a quarantine condition to users including senders and recipients of a mail system having at least one mailbox including hazard detection systems connected to a central server comprising:

detecting the presence of a mail piece in the mailbox;

detecting sender information from the mail piece;

testing the mail piece in the mailbox for hazards to determine an initial mail piece quarantine condition;

alerting the central server upon detection of a hazard and providing source information to the central server;

determining a notification method; and notifying at least one user of the mail piece quarantine using the sender information.

11. The method of claim 10 wherein the sender information includes detecting a destination address.

12. The method of claim 10 wherein the sender information includes detecting a return address.

13. The method of claim 10 wherein the sender information includes detecting a meter number.

14. The method of claim 10 further comprising:

storing a plurality of sender information records relating to a plurality of mail pieces placed in the at least one mailbox; and if the initial mail piece quarantine condition is detected, notifying at least two users indicated by the plurality of sender information records.

15. The method of claim 3 wherein the sender information comprises a meter number.

16. The method of claim 3 further comprising:

scanning the mail piece to obtain recipient information.

17. The method of claim 3 further comprising:

detecting destination information from the mail piece.

* * * * *